US00PP25215P3

(12) United States Plant Patent
Pavlich

(10) Patent No.: US PP25,215 P3
(45) Date of Patent: Jan. 6, 2015

(54) ***BEGONIA* PLANT NAMED 'GARDEN ANGEL BLUSH'**

(50) Latin Name: ***Begonia* hybrid**
Varietal Denomination: Garden Angel Blush

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 97 days.

(21) Appl. No.: 13/986,504

(22) Filed: May 9, 2013

(65) Prior Publication Data

US 2014/0338084 P1 Nov. 13, 2014

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Annette Para
(74) *Attorney, Agent, or Firm* — Klarquist Sparkman, LLP

(57) ABSTRACT

A new and distinct form of *Begonia* plant characterized by maple-like palmately lobed leaves with showy interveinal silvering blushed with plum-red, red leaf backs, a bushy habit, small clusters of large cherry pink flowers in winter to early spring, hardy to USDA Z7, and excellent vigor.

1 Drawing Sheet

Botanical denomination: *Begonia* hybrid.

Variety designation: 'Garden Angel Blush'.

Parentage: *Begonia* 'Benitochiba'×*Begonia grandis* subsp. *evansiana.*

Comparison to siblings *Begonia* 'Garden Angel Plum' and *Begonia* 'Garden Angel Silver' U.S. application Ser. No. 13/986,505.

BACKGROUND OF THE INVENTION

The present invention relates to a new and distinct cultivar of *Begonia*, of the family Begoniaceae, and given the cultivar name, 'Garden Angel Blush'. This plant originated from planned breeding program for a colorful series of landscape *Begonia.* The new cultivar originated from a cross between *Begonia* 'Benitochiba' (unpatented), as the seed parent, and *Begonia grandis* subsp. *evansiana,* as the pollen parent (unpatented). This selection is uniquely characterized by:

1. maple-like palmately lobed leaves with showy interveinal silvering blushed with plum-red,
2. red leaf backs,
3. a bushy habit,
4. small clusters of large cherry pink flowers in winter to early spring,
5. hardy to USDA Z7, and
6. excellent vigor.

Compared to the seed parent *Begonia* 'Benitochiba', an unpatented plant, the new cultivar has leaves that are palmately lobed rather than palmately compound. The new cultivar is hardy rather than being a tropical plant.

Compared to the pollen parent, *Begonia grandis* subsp. *evansiana* (an unpatented plant with the common name, Hardy *Begonia*), the new cultivar has leaves that are palmately lobed rather than no lobes and with strong interveinal silvering rather than no silvering.

Compared to *Begonia* 'Garden Angel Plum' (U.S. Plant patent application Ser. No. 13/986,507), the new cultivar has a plum-red blush rather than being all plum in warm temperatures and is shorter.

Compared to *Begonia* 'Garden Angel Silver' (U.S. Plant patent application Ser. No. 13/986,505), the new cultivar has a plum-red blush.

The new variety has been reproduced only by asexual propagation (cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a 9-month-old plant with flowers growing in a one gallon container in January in a warm greenhouse in Canby. Oreg.

DETAILED PLANT DESCRIPTION

The following is a detailed description of the new *Begonia* cultivar based on observations of nine-month-old specimens grown in one gallon containers inside a cool greenhouse in early January in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type.*—Herbaceous rhizomatous perennial.

*Form.*—Caulescent, shrubby.

*Cold hardiness.*—USDA Zone 7.

*Size.*—Grows to 35 cm tall and 60 cm wide.

*Vigor.*—Excellent.

Stem:

*Type.*—Upright.

*Size.*—Grows to 26 cm long and 8 mm wide.

*Internodes.*—From 2 cm to 7 cm long.

*Surface.*—Pubescent.

*Color.*—Greyed Purple 187A.

Leaf:

*Type.*—Simple.

*Arrangement.*—Alternate.

*Shape.*—Broadly ovate.

*Lobing/division.*—4 to 6 main palmate lobes.

*Margins.*—Serrate.

*Venation.*—Palmate, Gray Brown 199A on topside, bottom side Greyed Purple 187B.

*Apex.*—Acuminate.

*Base.*—Oblique.

*Blade size.*—Grows to 10.5 cm wide and 15 cm long.

*Surface texture.*—Pubescent on top and bottom.

*Stipules.*—Deciduous, ovate-lanceolate, grows to 19 mm long and 6 mm wide, papery, translucent, glabrous on both sides, Greyed Red 182C.

*Petiole description.*—Grows to 13 cm long and 6 mm wide, pubescent, Greyed Brown N199A.

*Leaf color.*—Top side between Greyed Purple N187A and N187B tinted Purple N79B except along veins where Black 203A; bottom side Red Purple 59A.

Inflorescence:

*Type.*—Axillary, bisexual, cymose.

*Number of flowers per cyme.*—About 4.

*Peduncle description.*—Grows 12 cm long and 2 mm wide, glabrous, fleshy, Greyed Brown 199B; with 2 opposite, dehiscent petiolate leaf-bracts below each cyme, which grow to 8 mm wide and 22 mm long, margins entire, tip apiculate, both sides glabrous Greyed Purple 185C.

*Pedicel description.*—Grow to 30 mm long, 1.5 mm wide, fleshy, pubescent, Red Purple 63C on staminate and pistillate flowers.

*Bloom period.*—Late fall to early winter in Canby, Oreg.

Flower bud:

*Size.*—Staminate flowers 25 mm long and 26 mm wide prior to opening; pistillate flowers are 17 mm deep and 12 mm wide prior to opening.

*Color.*—Red Purple 63A on tepal area, Red 48A on ovary.

Flower:

*Type.*—Monoecious, bilaterally symmetrical.

*Pistillate flower.*—Grows to 30 mm deep and 50 mm wide overall; 5 fleshy tepals, grow to 26 mm long and 19 mm wide, broadly elliptical, tip acute, base attenuate, margins entire, glabrous on inside and pubescent on outside, Red Purple 63C on both sides; ovary to 30 mm wide and 17 mm deep, three winged, two equal and one longer, Red 37A, style 7 mm long and 3 to 4 mm wide, Orange 26C, stigma 3 branched and twisted, stigma 6 mm deep and 10 mm wide overall, Orange 25C with edges Yellow 13C.

*Staminate flower.*—12 mm deep and 53 mm wide, 4 tepals, 2 larger outer tepals grow to 28 mm long and 20 mm wide, ovate, margin entire, tip obtuse, base cuneate; inner tepals grow to 22 mm long and 11 mm wide, oblanceolate, entire, tip obtuse, base attenuate; tepals both sides Red Purple 63C; stamen many in a globular head 7 mm in diameter on staminal column 2 mm long and 1 mm wide, Red 37C; filaments thread-like and 2.5 mm long, Green Yellow 1D, anthers 1.5 mm long, anthers Yellow 15D, no pollen.

*Fragrance.*—None.

*Lastingness.*—A cyme blooms for about 4 weeks on the plant.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

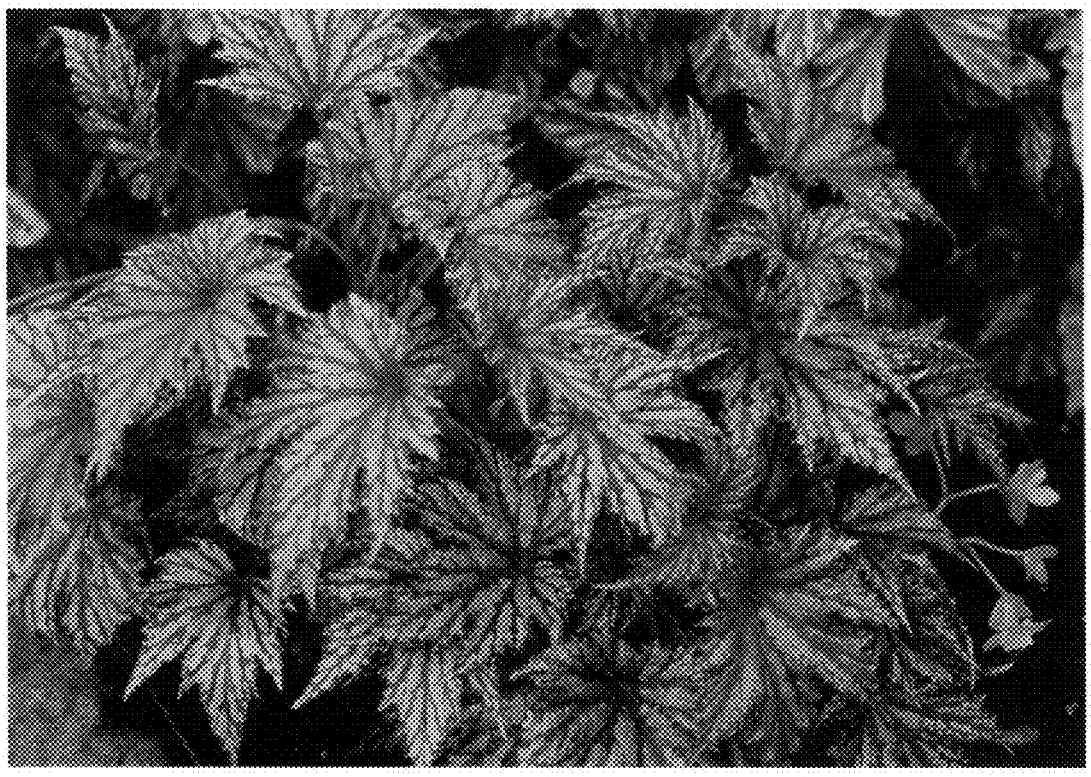

* * * * *